(12) United States Patent
Schwartz et al.

(10) Patent No.: US 6,508,821 B1
(45) Date of Patent: Jan. 21, 2003

(54) SOFT TISSUE REPAIR MATERIAL FIXATION APPARATUS AND METHOD

(75) Inventors: Herbert E. Schwartz, Fort Wayne, IN (US); Pamela Plouhar, South Bend, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/494,741

(22) Filed: Jan. 28, 2000

(51) Int. Cl.[7] .............................................. A61B 17/04
(52) U.S. Cl. ......................... 606/148; 606/104; 606/232
(58) Field of Search ........................... 606/104, 72, 148, 606/232; 411/457, 371.2, 372.6, 486, 473, 510, 923

(56) References Cited

U.S. PATENT DOCUMENTS

| | | | | |
|---|---|---|---|---|
| 1,396,238 A | * | 11/1921 | Watt | 411/371.2 |
| 1,435,134 A | * | 11/1922 | Boley | 411/372.6 |
| 1,932,036 A | * | 10/1933 | Gibson | 411/372.6 |
| 2,511,051 A | * | 6/1950 | Dzus | 411/923 |
| 2,564,176 A | * | 8/1951 | Rublee | 411/486 |
| 2,818,763 A | * | 1/1958 | Dunlap | 411/372.6 |
| 4,653,486 A | * | 3/1987 | Coker | 411/394 |
| 4,955,813 A | * | 9/1990 | Fochler | 411/457 |
| 5,261,914 A | * | 11/1993 | Warren | 606/73 |
| 5,667,513 A | * | 9/1997 | Torrie et al. | 606/104 |
| 5,720,753 A | * | 2/1998 | Sander et al. | 606/104 |
| 5,972,385 A | | 10/1999 | Liu et al. | 424/486 |

* cited by examiner

Primary Examiner—Gary Jackson
(74) Attorney, Agent, or Firm—Maginot, Moore & Bowman (57) ABSTRACT

An apparatus for use in affixing material to a location under repair includes a material retention member and an anchor. The anchor is configured to be inserted into a cavity in bone tissue, the anchor having a first end and a second end. The anchor also includes one or more raised ribs. The material retention member extends radially from the first end of the anchor in a plurality of directions, the material retention member including at least one contact surface adapted to exert a retention force on material that is interposed between the material retention device and the bone tissue.

28 Claims, 8 Drawing Sheets

SOFT TISSUE REPAIR MATERIAL FIXATION APPARATUS AND METHOD

BACKGROUND AND SUMMARY OF THE INVENTION

The present invention relates to assemblies that are used in the repair of bone and/or cartilage, and more particularly, to such assemblies as well as methods and apparatus for affixing repair material to bone and/or cartilage.

In the practice of orthopedics it is known to introduce repair material to a bone and/or cartilage requiring therapeutic tissue repair. Such repair material may include cartilage replacement material. In general, the repair materials currently employed in such circumstances include any of a collagen mix, a synthetic scaffold, a biologic scaffold, and nonwoven or woven fibers. In some cases, the repair material may include or comprise a flap of the damaged cartilage.

Currently, such repair materials are introduced to the location under repair and secured in the area via stapling to the bone tissue or via suturing. There is a need, however for a more secure method of affixing repair material to the location of the body under cartilage and/or bone repair.

The present invention fulfills the above needs, as well as others, by providing an apparatus for securing soft tissue repair material in a location in the body under repair. The apparatus includes an anchor and a material retention member that extends radially in a plurality of directions from the anchor and is adapted to exert a retaining force on the soft tissue repair material that urges or retains the material against bone tissue in the location under repair. One benefit of the present invention is that the anchor provides a mechanism by which the retention member may be anchored in place, allowing the retention member to retain the soft tissue repair material.

In a first embodiment of the present invention, an apparatus for use in affixing material to a location under repair includes a material retention member and an anchor. The anchor is configured to be inserted into a cavity in bone tissue, the anchor having a first end and a second end. The anchor also includes one or more raised ribs. The material retention member extends radially from the first end of the anchor in a plurality of directions, the material retention member including at least one contact surface adapted to exert a retention force on material that is interposed between the material retention device and the bone tissue.

In a second embodiment of the present invention, a method of effecting therapeutic reparation of a location of the body includes a first step disposing soft tissue repair material in the location of the body. The method also includes the step of securing an anchor of a fixation device into a cavity in bone tissue in the vicinity of the location, the anchor having a first end and a second end and further comprising a material retention member extending radially from the anchor in a plurality of directions. The anchor is secured into the cavity such that at least one contact surface of the material retention member engages a portion of the soft tissue repair material that is interposed between the material retention device and the bone tissue.

The above-described features and advantages, as well as others, will become more readily apparent to those of ordinary skill in the art by reference to the following detailed description and accompanying drawings.

DETAILED DESCRIPTION

Figure 1:
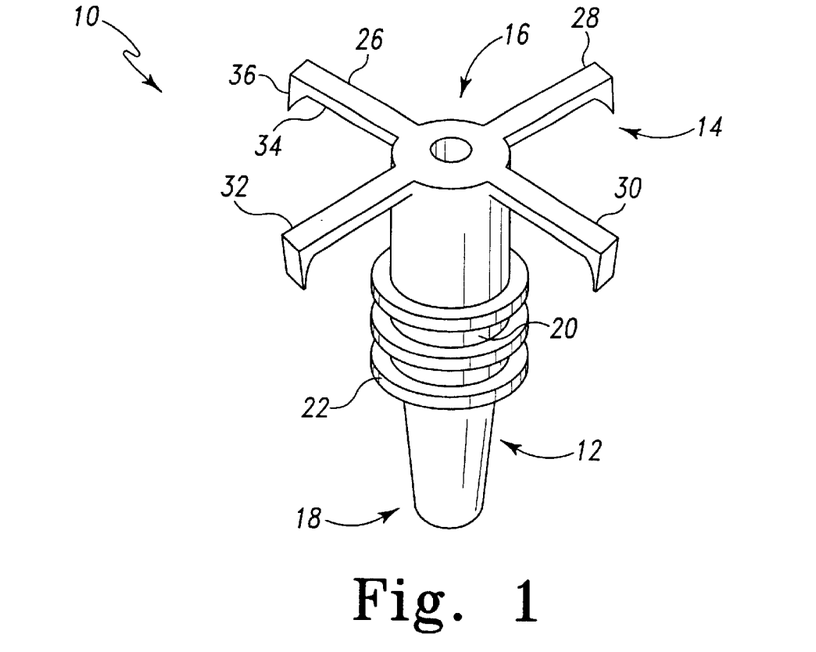
FIG. 1 shows a perspective view of a first exemplary embodiment of a fixation device according to the present invention.
Figure 1A:
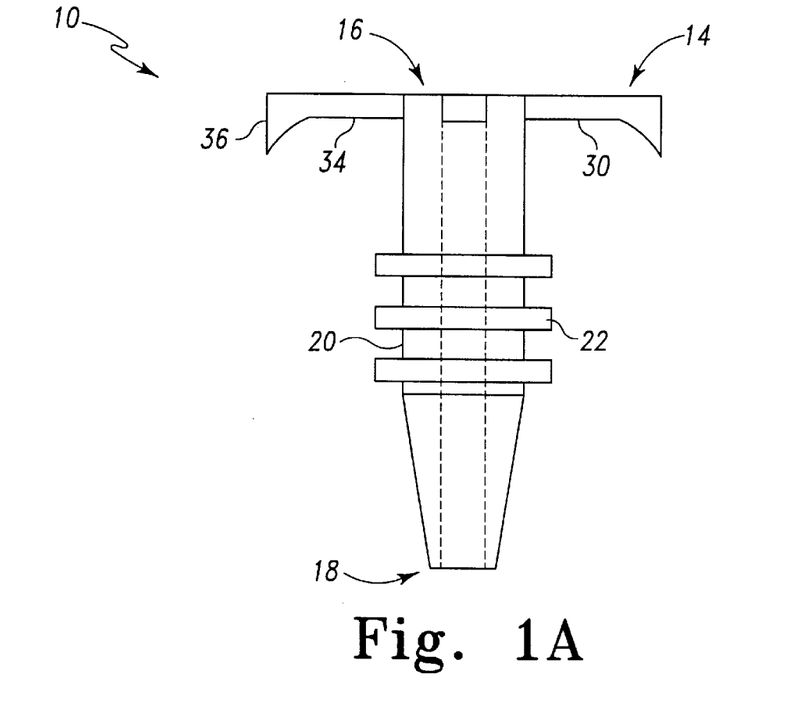
FIG. 1A shows a side plan view of the fixation device of FIG. 1.

FIG. 1 shows a perspective view of a first exemplary embodiment of a fixation device 10 according to the present invention. In general, the fixation device 10 includes an anchor 12 and a material retention member 14. The anchor 12 has a first end 16 and a second end 18. The material retention member 14 extends radially in a plurality of directions from the first end 16 of the anchor 12 and is configured to exert a retention force on material that is interposed between the material retention member 14 and bone tissue of a body. (See generally FIG. 2, discussed below). The fixation device 10 is preferably composed of polydioxanon, also referred to as PDS.

In further detail, the anchor 12 of the exemplary embodiment of FIG. 1 is in the form of a shaft and includes a cylindrical center portion 20 that has a plurality of raised ribs 22. Each of the plurality of raised ribs 22 extend circumferentially around the cylindrical center portion 20. The anchor 12 tapers inward from the cylindrical center portion 20 to the second end 18. The anchor 12 is cannulated, thereby forming a channel 24 within the anchor 12 that runs essentially the length of the anchor 12.

The material retention member 14 of the exemplary embodiment of FIG. 1 includes a plurality of spokes 26, 28, 30 and 32 that extend radially from the anchor in a plurality of directions. The spoke 26 includes a contact surface 34 that contacts the repair material (see FIG. 2) to exert downward force thereon. The contact surface 34 further includes a spike 36 extending axially therefrom. Each of the other spokes 28, 30 and 32 has a substantially similar structure.

Figure 2:
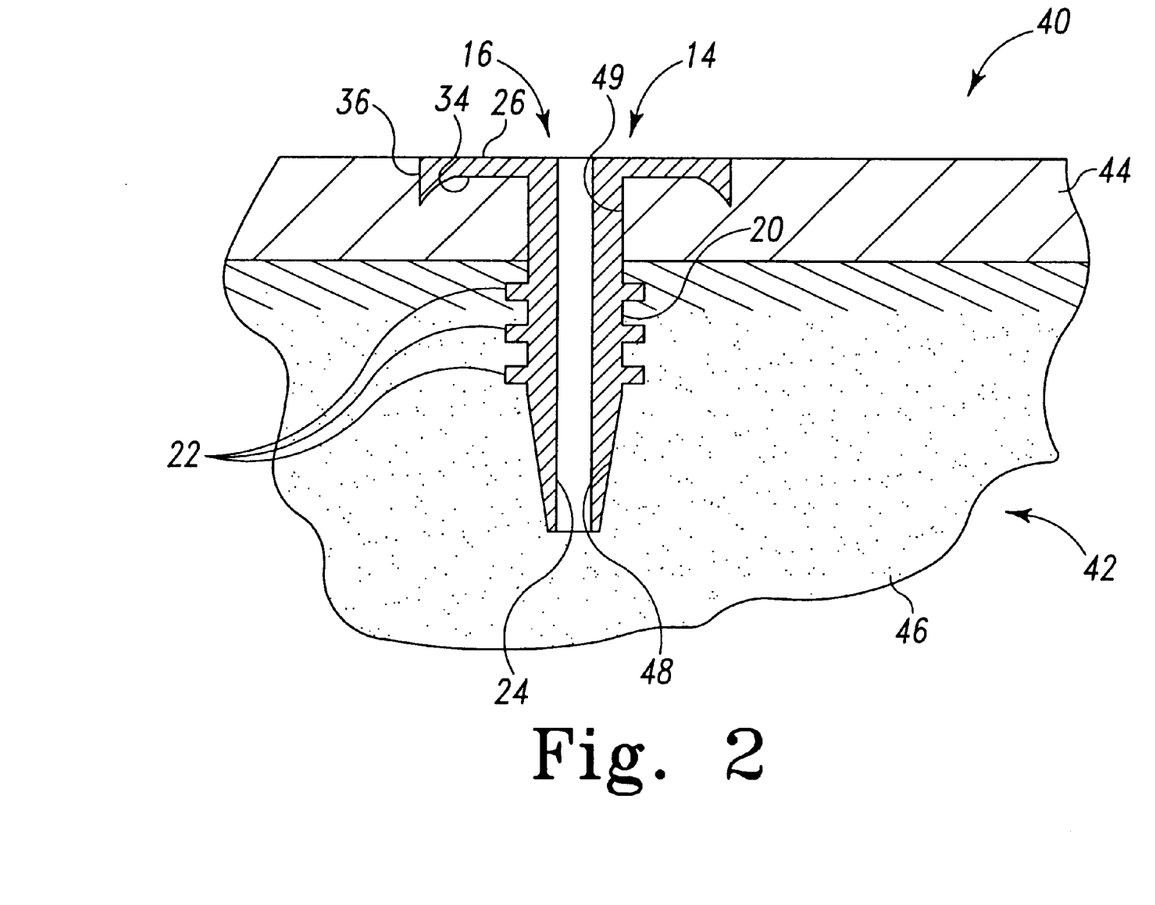
FIG. 2 shows a side cutaway view of a first exemplary embodiment of an assembly for effecting therapeutic repairs that includes the fixation device of FIG. 1 shown implemented in a location of a body that is under repair.

A generalized discussion of the use of the retention device 10 in effecting therapeutic repair of a location in the body is provided below. FIGS. 1 and 2 will be referenced in the generalized discussion of the use of the retention device 10.

FIG. 2 shows a side cutaway view of a first exemplary embodiment of an assembly 40 for effecting therapeutic repairs that includes the fixation device 10 of FIG. 1. The assembly 40 is shown implemented in a location 42 of a body that is under repair. In general, the location 42 of the body, which may be human or otherwise, is in the vicinity of bone tissue. In the preferred embodiment of the present, the invention, the assembly 40 is used to effect therapeutic repairs to locations near bone tissue that have damaged or removed cartilage. Typically, damaged or removed cartilage occurs near bone joints such as, for example, in the vicinity of a human knee, ankle or wrist.

The repair assembly 40 includes a soft tissue repair material 44, which in the preferred embodiment is a matrix, that is secured to bone tissue 46 in the location 42 that is exposed due to cartilage removal or damage. The repair material 44 is secured to the bone tissue 46 at least in part by the fixation device 10. To this end, the material retention member 14 is positioned to exert a retention force on the repair material in the direction toward the bone tissue 46.

It will be noted that the repair material 44 may be secured to the bone tissue by fixation devices other than the fixation device 10 of FIGS. 1 and 2. Such other fixation devices may include those shown in FIGS. 4 through 10 or other suitable alternative devices that include an anchor and a material retention member that extends in a plurality of directions from the anchor. Such devices would have at least some of the benefits of the invention provided herein, including retention strength and reliability.

The soft tissue repair material 44 may be composed of any one of a plurality of materials known to be used for cartilage repair. Such materials include, but are not limited to, a collagen matrix, a synthetic scaffold, a biologic scaffold, nonwoven fibers or woven fibers. The preparation and use of such materials in connection with cartilage replacement and repair is known.

In order to effect a therapeutic repair, a cavity 48 is formed in the bone tissue proximate to the location 42 of the body. The cavity 48 is preferably sized to accept the middle portion 20 and the second end 18 of the anchor 12 in a relatively tight fit. Preferably, the cavity 48 has a length exceeding its diameter. The diameter of the cavity 48 may suitably be on the order of 1 mm to 2 mm (pre-taper) for use in human applications. The cavity 48 may be formed with using a pin, not shown, inserted and manipulated arthroscopically. The pin diameter should be approximately equal to or slightly smaller than the diameter of the anchor 12.

In a preferred operation, the soft tissue repair material 44 is disposed in the location 42 at the same time that the fixation device 10 is secured to the bone tissue 46. However, it will be noted that the soft tissue repair material 44 may be disposed in the location 42 before insertion of the fixation device 10 and, in some cases, prior to forming the cavity 48.

Returning to the preferred operation, a core 49 is formed in the soft tissue repair material 44 prior to insertion. The core 49 is sized to receive anchor 12 of the fixation device 10. Coring the repair material 44 avoids potential damage caused by a forced insertion of the second end 18 and middle portion 20 of the anchor 12 through the repair material 44. Once cored, the soft tissue repair material 44 is inserted onto the anchor 12, and the anchor 12 is inserted onto a pin, not shown, which is sized to fit through the channel 24. The anchor 12 and soft tissue repair material 44 may then be advanced along the pin through a cannula or the like to the location 42. The pin may be used as is well known in the art to guide the anchor 12 to the cavity 48. A slide hammer, not shown, may then be used to advance the second end 18 of the anchor 12 into the cavity 48 while the repair material 44 is trapped or retained in the location 42 by the material retention member 14.

In any event, the anchor 12 is advanced forward into the cavity 38 until the raised ribs 22 are disposed at least partially within the cavity 38. The raised ribs 22 and the bone tissue 46 cooperatively deform to form an interlock therebetween. The interlock assists in resisting inadvertent dislodge of the anchor 12. Moreover, as the bone tissue 46 heals, it will grow into cavities formed by successive raised ribs 22, thereby further decreasing the possibility of inadvertent dislodge. However, it will be noted that the raised ribs 22 are not necessary to achieve attachment of the repair material 44 via the fixation device 10. An anchor comprised of a non-ribbed shaft provides a secure attachment to the bone tissue through frictional forces. Nevertheless, the inclusion of the raised ribs 22 increase the robustness of the attachment for the reasons discussed above.

Thus, the present invention provides a reliable method of affixing soft tissue repair material to a location of the body under theurapeutic repair. Specifically, the use of a material retention member that engages the repair material 44 in a plurality of directions provides an increased and dispersed surface area of the repair material 44 that is subject to the retention force. Such dispersion of the surface area under retention force increases the ability to retain the repair material 44 and avoid slip-through and dislodge of the repair material. It can be observed that the dispersion of the surface area of the repair material under force may be increased by increasing the length of the spokes 26, 28, 30, and 32. However, excessive spoke length increases the possibility of shearing the spokes 26, 28, 30 and 32. Spoke lengths exceeding $\frac{1}{4}^{th}$ of the length of the anchor 12, and preferably on the order of $\frac{1}{2}^{th}$ of the length of the anchor 12 or more, provide advantageous dispersion of the surface area of the repair material 44 that is under force.

As discussed above, the fixation device 10 in at least some embodiments is amenable to insertion using arthroscopic techniques and instruments. To this and other ends, the anchor 12 preferably has a length of on the order of 12 mm to 20 mm. In a preferred embodiment, the length of the spoke 26 is preferably 6 mm to 8 mm, as measured from the center of the anchor 12.

In some circumstances, the quantity of soft tissue repair material, and more particularly, the surface area of the repair material, exceeds that which can be reasonably secured by a single fixation device. In such circumstances, a plurality of fixation devices similar to the fixation device may be employed in connection with a location under repair.

Figure 3:
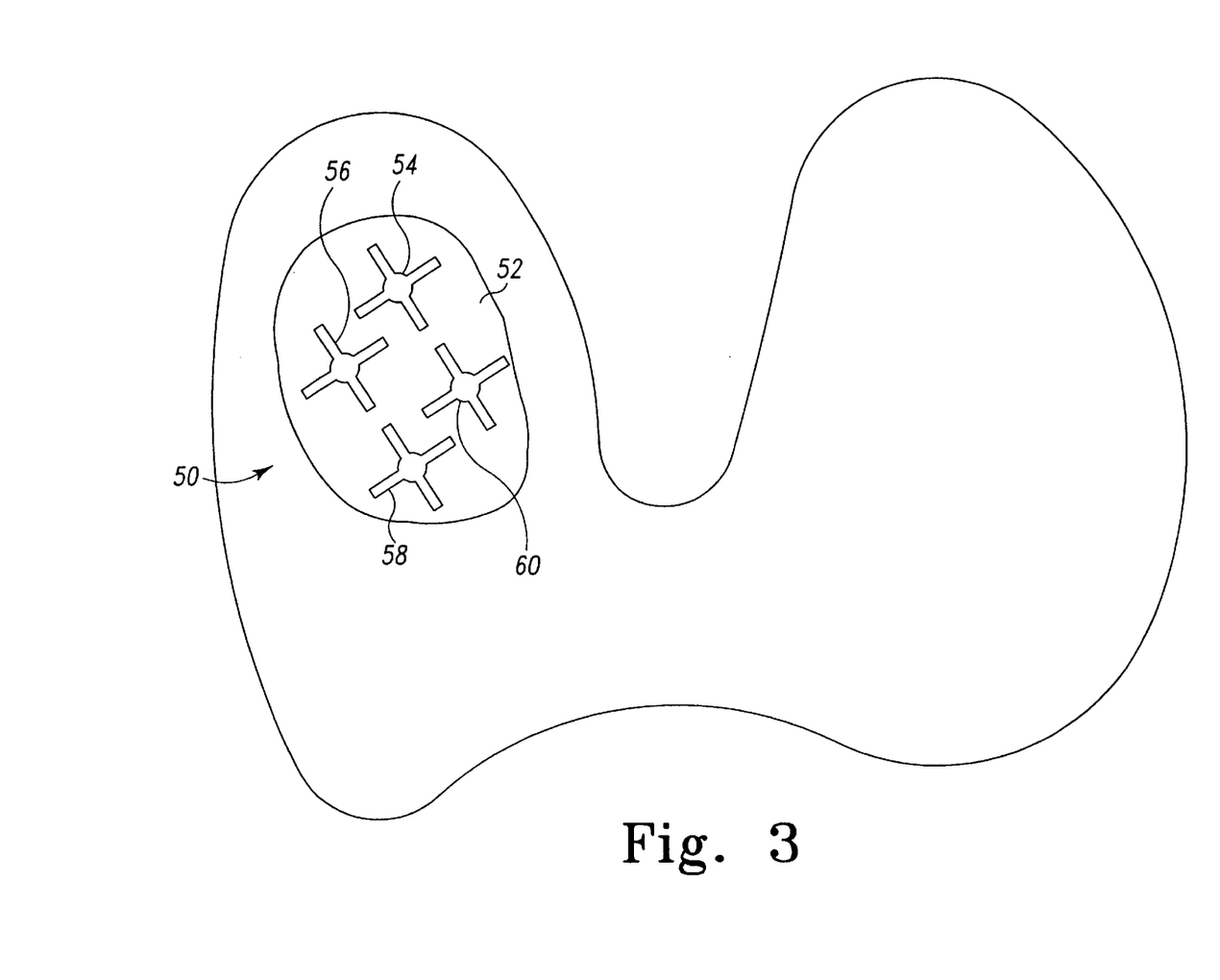
FIG. 3 shows a top plan view of a second exemplary embodiment of an assembly for affecting therapeutic repairs.

FIG. 3 shows a top plan view of a second exemplary embodiment of an assembly 50 for affecting therapeutic repairs wherein the amount of repair material 52 exceeds that which may reasonably be secured using a single fixation device. The assembly 50 includes a relatively large quantity (as opposed to the quantity shown in FIG. 2) of repair material 52 and a plurality of fixation devices 54, 56, 58, and 60. The plurality of fixation devices 54, 56, 58, and 60 may suitably have the structure of the fixation device 10 of FIG. 1 as well as any other fixation device according to the present invention. Each of the plurality of fixation devices 54, 56, 58 and 60 are inserted into cavities similar to the cavity 48. It is readily apparent that as many or as few fixation devices may be employed as is necessary to achieve an appropriate amount of retention strength.

Figure 4:
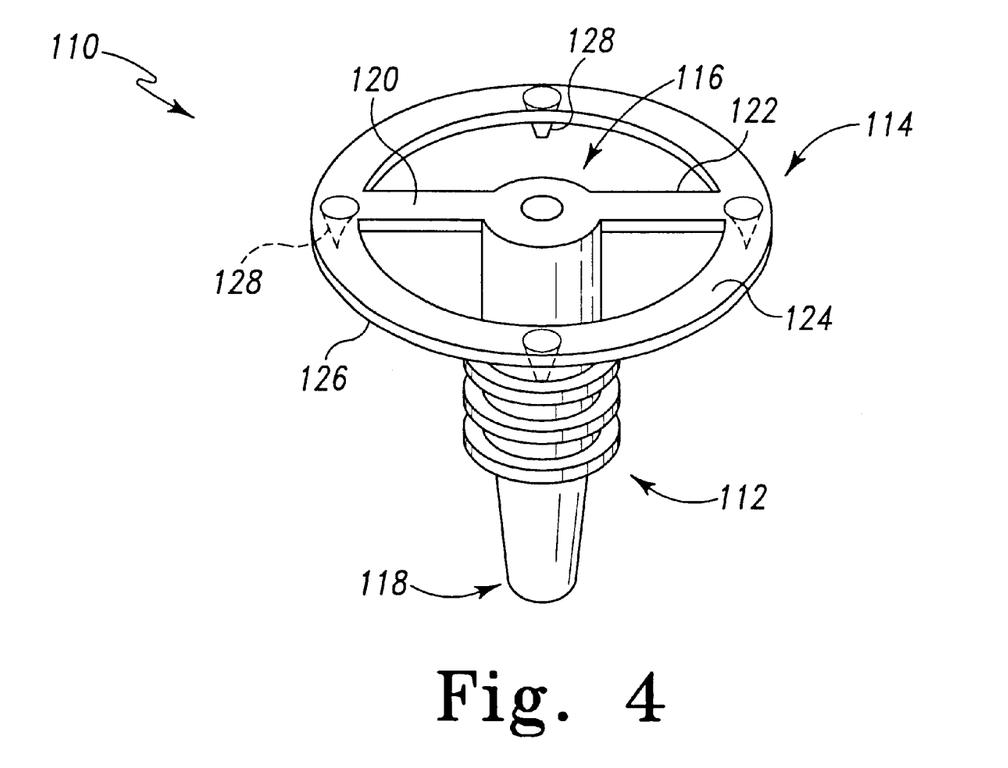
FIG. 4 shows a side plan view of a second exemplary embodiment of a fixation device according to the present invention.

It is noted that other embodiments of a fixation device according to the present invention may provide alternative or additional benefits. For example, FIG. 4 shows a second exemplary embodiment of a fixation device 110 according to the present invention. The fixation device 110 includes an anchor 112 similar to the anchor 12 of FIG. 1 and a material retention member 114. The anchor 112, similar to the anchor 12, includes a first end 116 and a second end 118.

The material retention member 114 of the second exemplary embodiment of the fixation device 110 includes first and second spokes 120 and 122 which extend in opposing radial directions. Each of the first and second spokes 120 and 122 terminates at a connection point to a loop member 124. The loop member 124, which in the exemplary embodiment described herein is in the form of a circular ring, extends around the first end 116. The loop member 124 includes a contact surface 126 which corresponding extends around the first end 116. The loop member further includes a plurality of spikes 128 extending downward from the contact surface 126.

One advantage of the loop member 124 is that the pressure points exerted by the material retention member 114 form a continuous loop, as opposed to discontinuous points, which further decreases the potential of tearing the repair material, not shown. Consistent with the embodiment described above, the length of the spokes 120 and 122 (and thus the radius of the loop member 124) is preferably between $1/4^{th}$ and $1/2^{th}$ of the length of the anchor 112.

In some circumstances, the bone tissue at the location of the body in which the repair must be effectuated is concave in shape. As such, it is advantageous to provide a fixation device having a material retention device that extends in a generally convex manner with respect to the repair material so that it conforms to the shape of the underlying bone tissue.

Figure 5:
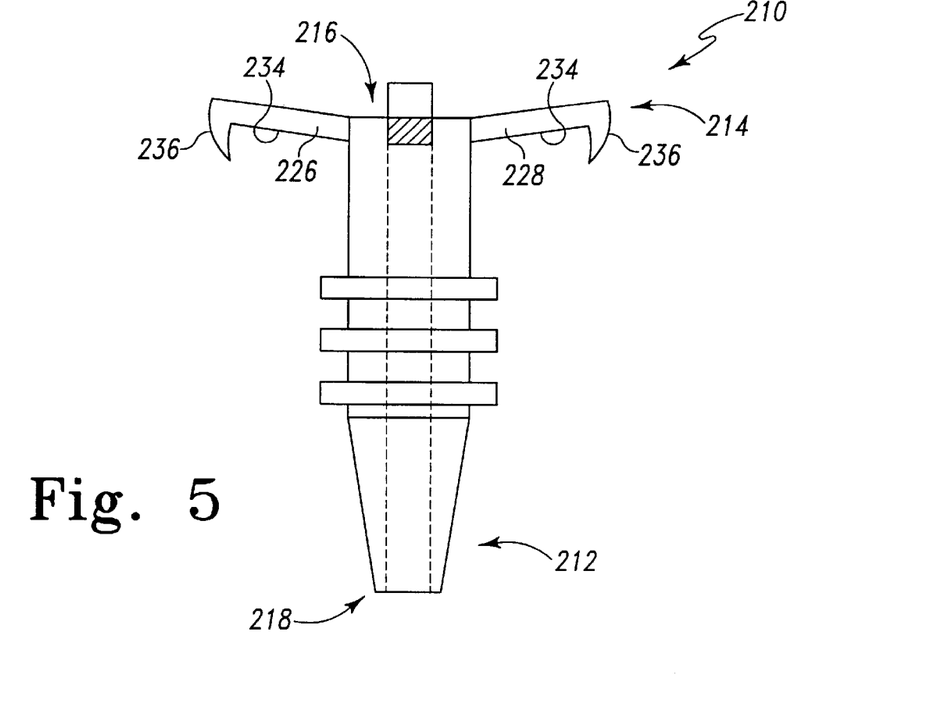
FIG. 5 shows a side plan view of a third exemplary embodiment of a fixation device according to the present invention.

To this end, FIG. 5 shows a side plan view of a third exemplary embodiment of a fixation device 210 according to the present invention which incorporates a convex material retention device 214. Again, the fixation device 210 includes an anchor 212 and the material retention member 214. The anchor 212 has a first end 216 and a second end 218. The material retention member 214 extends radially in a plurality of directions from the first end 216 of the anchor 212 and furthermore extends at a non-normal angle upward with respect to an axis of the anchor portion.

The material retention member 214 of the exemplary embodiment of FIG. 5 includes a plurality of spokes 226 and 228 (and typically will include more, not shown in this view) that extend radially and angularly from the anchor in a plurality of directions. The overall shape of the material retention member 214 is convex with respect to second end 218. Each of the spokes 226 and 228 includes a contact surface 234 that is configured to contact the repair material to exert downward force thereon. The contact surfaces 234 further include spike 236 extending axially therefrom.

Figure 6:
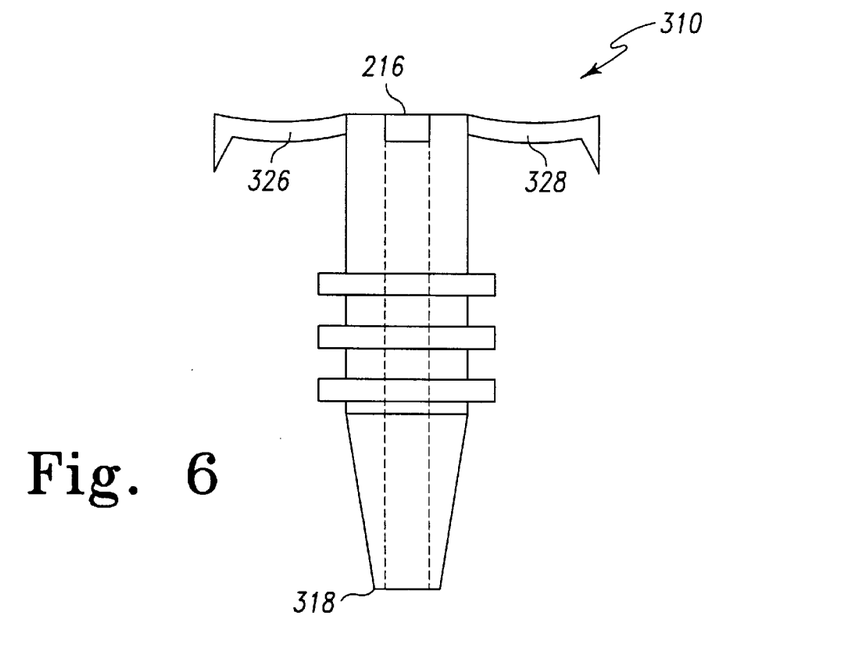
FIG. 6 shows a side plan view of a fourth exemplary embodiment of a fixation device according to the present invention.

FIG. 6 shows a side plan view of a fourth exemplary embodiment of a fixation device 310 according to the present invention. The fixation device 310 is identical to the fixation device 210 except for the spokes. The fixation device 310 includes a plurality of spokes, including the spokes 326 and 328 shown in FIG. 6, which are individually convex in shape from the point of view of the second end 318 of the anchor 312. The convex shape of the spokes 326 and 328 also help accommodate placement of the fixation device within concave shaped bone tissue.

Figure 7:
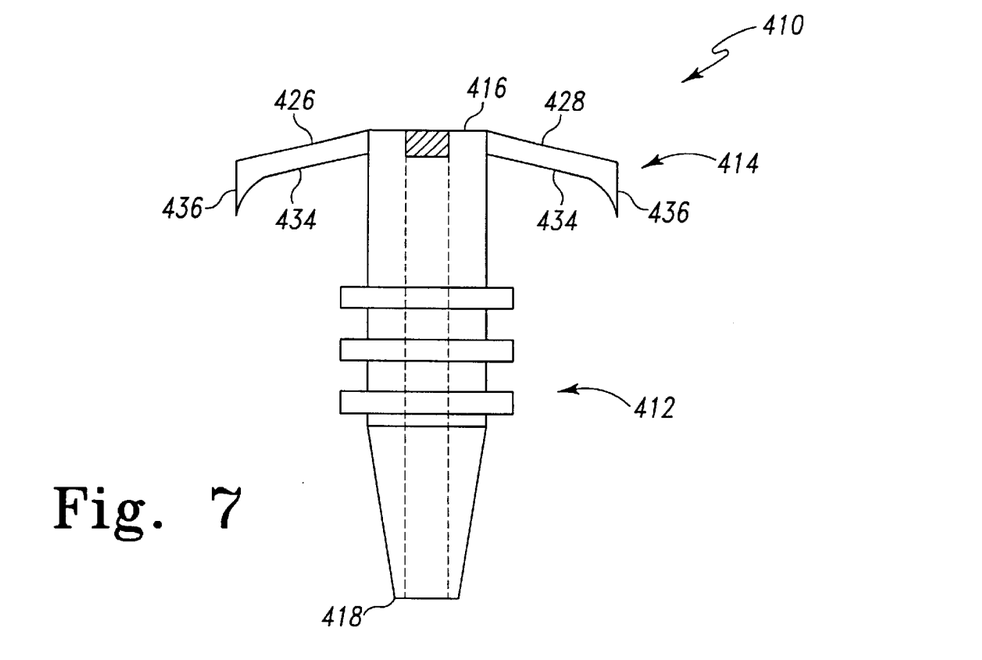
FIG. 7 shows a side plan view of a fifth exemplary embodiment of a fixation device according to the present invention.

FIG. 7 shows a side plan view of a fifth exemplary embodiment of a fixation device 410 according to the present invention which incorporates a concave material retention device 414. As above, the fixation device 410 includes an anchor 412 and the material retention member 414. The anchor 412 has a first end 416 and a second end 418. The material retention member 414 extends radially in a plurality of directions from the first end 416 of the anchor 412 and furthermore extends at a non-normal angle downward with respect to an axis of the anchor portion.

The material retention member 414 of the exemplary embodiment of FIG. 5 includes a plurality of spokes 426 and 428 (and typically will include more, not shown in this view) that extend radially and angularly from the anchor in a plurality of directions. The overall shape of the material retention member 414 is concave with respect to second end 418. Each of the spokes 426 and 428 includes a contact surface 434 that is configured to contact the repair material to exert downward force thereon. The contact surfaces 434 further include spikes 436 extending axially therefrom.

The concave material retention member 414 may be used to accommodate locations of the body under repair in which the relevant bone tissue is convex in shape. Alternatively, the concave material retention member 414 may be used as a spring bias force against the repair material when inserted. In particular, when the fixation device 410 is inserted into a cavity in bone tissue (see FIG. 2), the fixation device 410 may be continually advanced into the cavity until the spokes 426 and 428 are elastically deformed or spring-biased backward. As such, the inserted fixation device 410 may suitably appear as the fixation device 10 of FIG. 2, in other words, such that the spokes 426 and 428 extend in the normal plane with respect to the anchor, when fully inserted. In such a case, the fixation device 410 will exhibit a greater retention force on the repair material as a result of the spring bias of the spokes 426 and 428.

Figure 8:
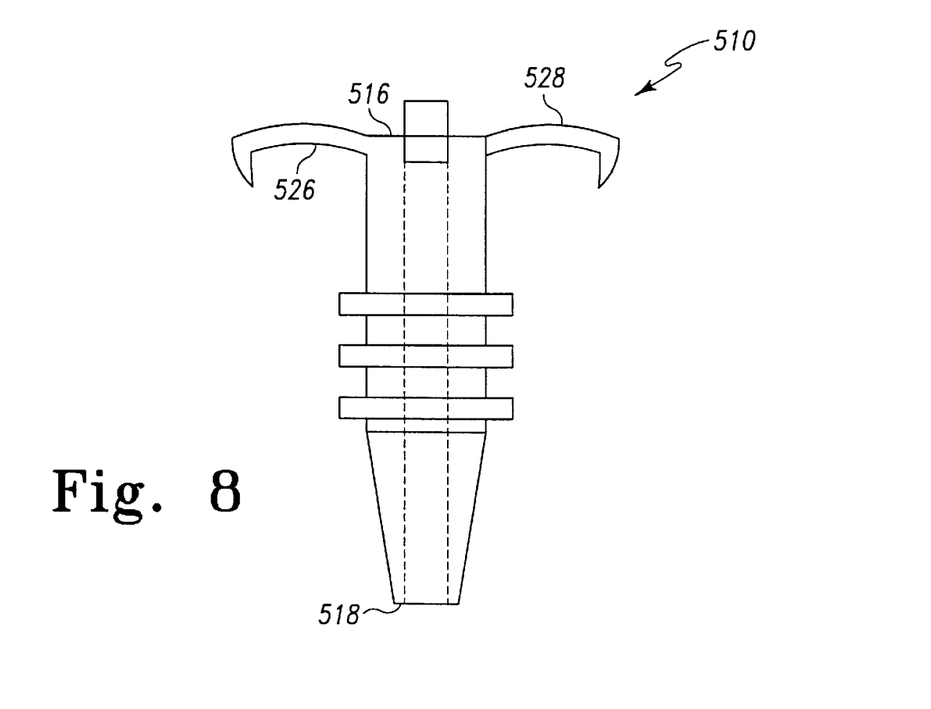
FIG. 8 shows a side plan view of a sixth exemplary embodiment of a fixation device according to the present invention.

Another embodiment that provides many of the advantages discussed above in connection with the fixation device 410 are provided by the fixation device 510 of FIG. 8. FIG. 8 shows a side plan view of a sixth exemplary embodiment of a fixation device 510 according to the present invention.

The fixation device 510 is identical to the fixation device 410 except for the spokes. The fixation device 510 includes a plurality of spokes, including the spokes 526 and 528 shown in FIG. 8, which are individually concave in shape from the point of view of the second end 518 of the anchor 512. The convex shape of the spokes 526 and 528 helps accommodate placement of the fixation device 510 within convex shaped bone tissue, and/or provides additional retention force via spring biasing.

Figure 9:
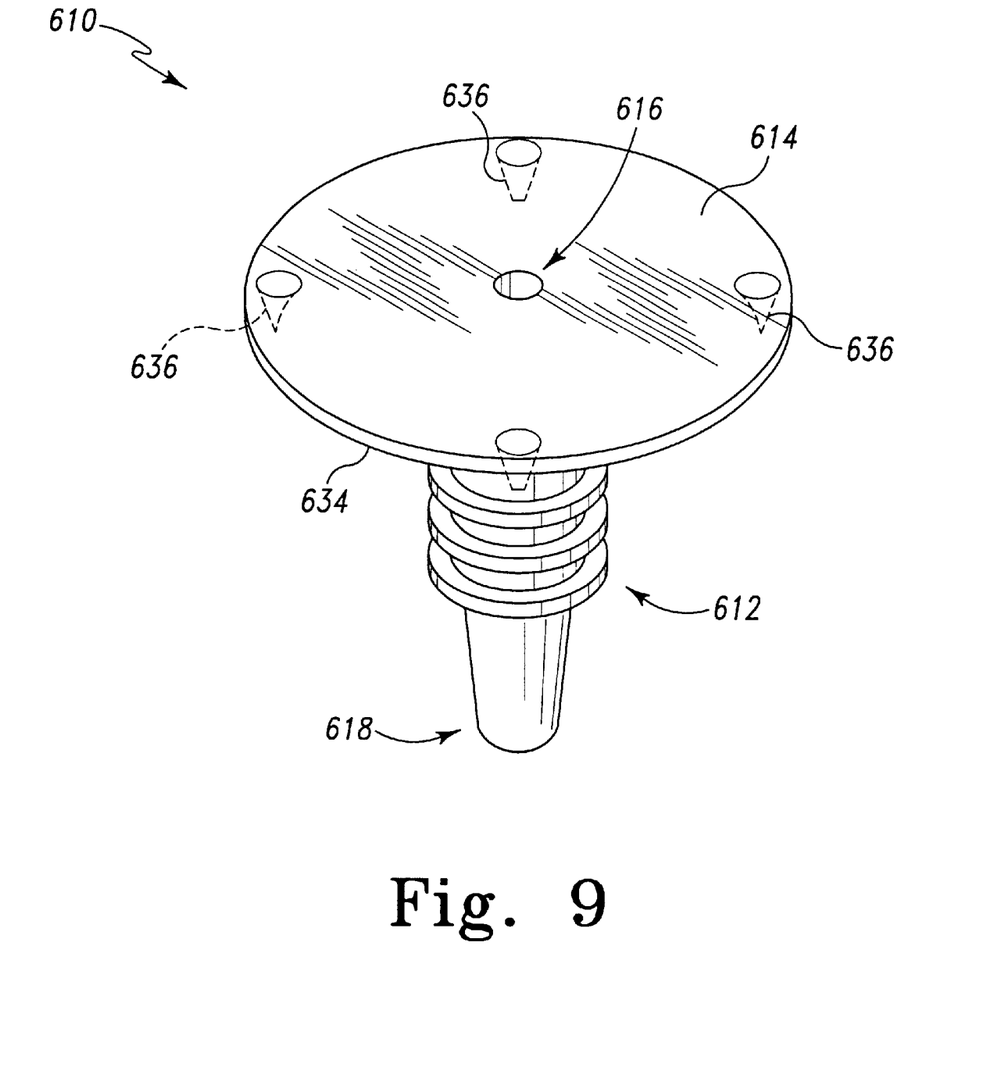
FIG. 9 shows a perspective view of a seventh exemplary embodiment of a fixation device according to the present invention.

FIG. 9 shows a perspective view of a seventh exemplary embodiment of a fixation device 610 according to the present invention that includes a substantially disk-shaped material retention member 614. The disk-shaped material retention member 614 provides similar advantages as those discussed above in connection with the loop member 124 of the fixation device 110 of FIG. 4. In an alternative embodiment, the top surface of the disk-shaped material retention member 614 may be convex or otherwise shaped to accommodated bone geometry in the location under repair. Specifically, the retention force exerted by the material retention member 610 is dispersed in a continuous manner.

In general, the fixation device 610 includes an anchor 612 and the material retention member 614. The anchor 612 has a first end 616 and a second end 618. The material retention member 614 comprises a disk that extends radially in a plurality of directions from the first end 616 of the anchor 612. The material retention member 614 includes a contact surface 634 that contacts the repair material (see FIG. 2) to exert downward force thereon. The contact surface 634 further includes a plurality of spikes 636 extending axially therefrom.

Figure 10:
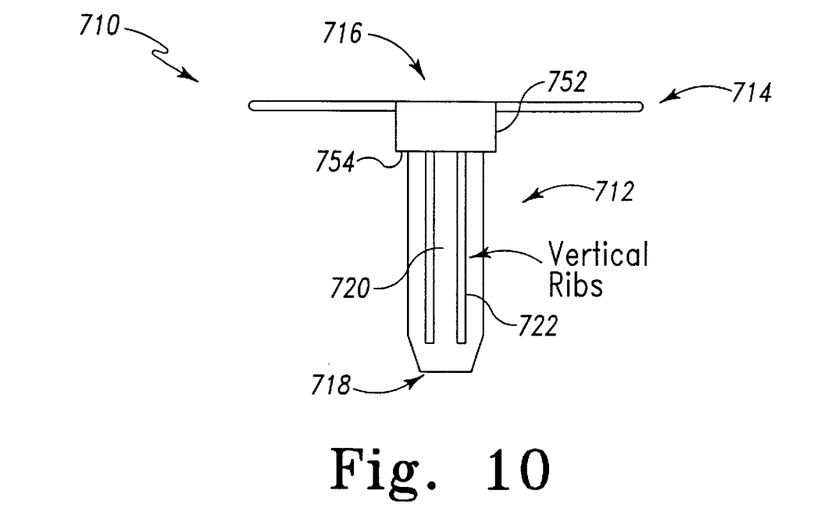
FIG. 10 shows a side plan view of an eighth exemplary embodiment of a fixation device according to the present invention.
Figure 11:
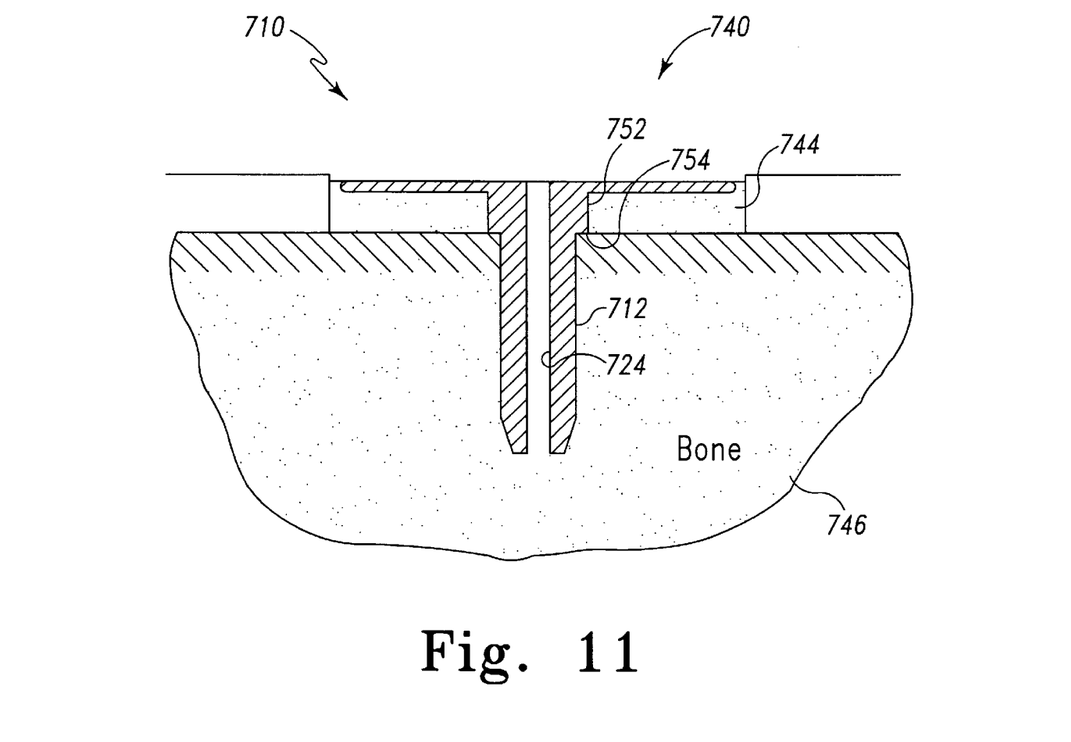
FIG. 11 shows a side cutaway view of a third exemplary embodiment of an assembly for effecting therapeutic repairs that includes the fixation device of FIG. 10 shown implemented in a location of a body that is under repair.

FIG. 10 shows a side plan view of an eighth exemplary embodiment of a fixation device 710 according to the present invention that provides two alternative advantages relating to resisting rotation and insertion of the fixation device into the repair material. FIG. 11 shows a side cutaway view of a third exemplary embodiment of an assembly 740 for effecting therapeutic repairs that includes the fixation device 710 of FIG. 10 shown implemented in a location 742 of a body that is under therapeutic repair. In general, the assembly 740 includes a quantity of soft tissue repair material 744 and the fixation device 710.

In general, the fixation device 710 includes an anchor 712 and a material retention member 714. The anchor 712 has a first end 716 and a second end 718. The material retention member 714 extends radially in a plurality of directions from the first end 716 of the anchor 712 and is configured to exert a retention force on repair material 744 that is interposed between the material retention member 714 and bone tissue 746 of a body.

In further detail, the anchor 712 of the exemplary embodiment of FIG. 10 is in the form of a shaft and includes a center portion 720. The center portion 720 includes a plurality of raised ribs 722. In particular, each of the plurality of raised ribs 722 extends axially or longitudinally along an outer surface of the center portion 720 of the anchor 720. The longitudinally disposed raised ribs 722 cooperate with the bone tissue 746 to form an interlock that resists rotation of the fixation device 710.

The anchor 712 is slightly chamfered at the second end 718. As above, the anchor 712 may suitably be cannulated, thereby forming a channel 724 within the anchor 712 that runs essentially the length of the anchor 712.

The anchor 712 furthermore includes a shoulder 752 that is has a radius that is wider than the center portion 720. The larger radius of the shoulder 752 forms a shelf surface 754 at the intersection of the shoulder and the center portion 720 that faces toward the second end 718 of the anchor 712. The shelf surface 754 provides a mechanism by which insertion of the anchor 712 may be stopped (see FIG. 11). As a result, the anchor 712 may be more precisely located at a particular depth within the bone tissue 746.

The material retention member 714 of the exemplary embodiment of FIG. 10 may suitably have a structure similar to that describe above in connection with any of the material retention members 14, 114, 214, 314, 414, 514 or 614.

It will be appreciated that the above described embodiments are merely exemplary, and that those of ordinary skill in the art may readily devise their own implementations of the present invention that incorporate the principles of the present invention and fall within the spirit and scope thereof. For example, the exact number of spokes in the various fixation devices need not be as shown in the exemplary embodiments discussed herein. Likewise, it is noted that at least some of the advantages of the raised ribs 22 and 722 described above may enjoyed in embodiments in which the raised ribs are raised from a center portion of the anchor that is narrower than the remainder of the anchor. In other words, the raised ribs and the remainder of the anchor form recessed channels between the raised ribs in the center portion. In such embodiments, the raised ribs may be created by merely removing material from the center portion of a smooth anchor shaft.

We claim:

1. An apparatus for use in affixing material to a location under repair, the apparatus comprising:
    an anchor configured to be inserted into a cavity in bone tissue, the anchor having a first end and a second end, the anchor having an exterior surface, the exterior surface including one or more raised ribs;
    a material retention member extending radially from the anchor in a plurality of directions, the material retention member including at least one contact surface adapted to exert a retention force on material that is interposed between the material retention member and the bone tissue, wherein the material retention device comprises a plurality of spokes extending radially from the anchor in a plurality of directions, each spoke including at least a portion of said at least one contact surface; and
    a loop member extending substantially around the first end of the anchor, the loop member coupled to the anchor via the plurality of spokes.

2. The apparatus of claim 1 wherein the loop member comprises a circular ring.

3. The apparatus of claim 1 wherein the loop member further comprises a plurality of spikes extending axially from said ring.

4. The apparatus of claim 1 wherein the one or more raised ribs extend circumferentially around at least a portion of the anchor.

5. The apparatus of claim 1 wherein the anchor comprises a shaft.

6. An assembly for use in effecting therapeutic reparation of a location of the body comprising, the assembly comprising:
    a quantity of soft tissue repair material; and
    a fixation device, the fixation device comprising
        an anchor configured to be inserted into a cavity in bone tissue, the anchor having a first end and a second end; and
        a material retention member extending radially from the anchor in a plurality of directions, the material retention member including at least one contact surface engaging at least a portion of the quantity of soft tissue repair material, wherein the material retention member comprises a plurality of spokes extending radially from the anchor in a plurality of directions, each spoke including at least a portion of said at least one contact surfaces; and
    a loop member extending substantially around the first end of the anchor, the loop member coupled to the anchor via the plurality of spokes.

7. The apparatus of claim 6 wherein the loop member comprises a circular ring.

8. The apparatus of claim 6 wherein the loop member further comprises a plurality of spikes extending axially from said ring.

9. The assembly of claim 6 wherein the material retention member terminates in each direction at a distance from the anchor exceeding one-fourth the length of the anchor.

10. The apparatus of claim 6 wherein the anchor further comprises raised ribs extending from an outer surface thereof.

11. The apparatus of claim 6 wherein the one or more raised ribs extend circumferentially around at least a portion of the anchor.

12. The apparatus of claim 6 wherein the anchor comprises a shaft.

13. The apparatus of claim 6 wherein the anchor is cannulated.

14. The assembly of claim 6 wherein the quantity of soft tissue repair material includes a matrix.

15. An apparatus for use in affixing material to a location under repair, the apparatus comprising:
   an anchor configured to be inserted into a cavity in bone tissue, the anchor having a first end and a second end;
   a material retention member extending radially from the first end of the anchor in a plurality of directions, the material retention member including a plurality of spikes extending therefrom and adapted to contact material that is interposed between the material retention device and the bone toward the second end of the anchor, wherein the material retention member terminates in each direction at a distance from the anchor exceeding one-fourth the length of the anchor and further wherein the material retention device comprises a plurality of spokes extending radially from the anchor in a plurality of directions; and
   a loop member extending substantially around the first end of the anchor, the loop member coupled to the anchor via the plurality of spokes.

16. The apparatus of claim 15 wherein said plurality of spikes extend from said loop member.

17. The apparatus of claim 15 wherein the anchor further includes one or more raised ribs extending from an outer surface thereof.

18. The apparatus of claim 15 wherein the anchor is cannulated.

19. The apparatus of claim 15 wherein the anchor defines a shaft.

20. An assembly for use in effecting therapeutic reparation of a location of the body, comprising:
   a quantity of soft tissue repair material; and
   a fixation device including (i) an anchor configured to be inserted into a cavity in bone tissue, and (ii) a plurality of spokes extending radially from said anchor in a plurality of directions, each of said plurality of spokes having a repair material contact portion spaced apart from said anchor which engages at least a portion of said quantity of soft tissue repair material,
   wherein each of said plurality of spokes terminates in each direction at a distance from said anchor exceeding one-fourth of a length of said anchor, and
   wherein each of said plurality of spokes is secured in a cantilevered manner to said anchor.

21. The apparatus of claim 20 wherein each of said plurality of spokes further includes at least one spike extending axially away from said spokes.

22. The apparatus of claim 20 wherein:
   said anchor has an exterior surface,
   said exterior surface possesses one or more raised ribs, and
   said one or more raised ribs extend circumferentially around at least a portion of said anchor.

23. The apparatus of claim 20, wherein:
   said anchor comprises an elongated shaft, and
   each of said plurality of spokes extends from a proximal end portion of said elongated shaft.

24. The apparatus of claim 20, wherein each of said plurality of spokes further extends at an angle from a plane that is normal to said anchor.

25. The apparatus of claim 20 wherein, each of said plurality of spokes extends in a concave manner with respect to said soft tissue repair material.

26. The apparatus of claim 20 wherein, each of said plurality of spokes extends in a convex manner with respect to said soft tissue repair material.

27. The apparatus of claim 20, wherein said anchor is cannulated.

28. The apparatus of claim 20, wherein:
   each said plurality of spokes possesses a first maximum width,
   said anchor possesses a second maximum width, and
   said first maximum width is less than said second maximum width.

* * * * *